(12) United States Patent
Griggio

(10) Patent No.: US 10,499,810 B2
(45) Date of Patent: Dec. 10, 2019

(54) APPARATUS FOR OCULAR FUNDUS INSPECTION

(71) Applicant: NEXT SIGHT S.R.L., Pordenone PN (IT)

(72) Inventor: Paola Griggio, Padua (IT)

(73) Assignee: NEXT SIGHT S.R.L., Pordenone PN (IT)

( * ) Notice: Subject to any disclaimer, the term of this patent is extended or adjusted under 35 U.S.C. 154(b) by 0 days.

(21) Appl. No.: 14/780,954

(22) PCT Filed: Mar. 28, 2014

(86) PCT No.: PCT/IT2014/000085
§ 371 (c)(1),
(2) Date: Sep. 28, 2015

(87) PCT Pub. No.: WO2014/155404
PCT Pub. Date: Oct. 2, 2014

(65) Prior Publication Data
US 2016/0051140 A1 Feb. 25, 2016

(30) Foreign Application Priority Data
Mar. 28, 2013 (IT) .............................. VI2013A0087

(51) Int. Cl.
  *A61B 3/12* (2006.01)
  *A61B 3/00* (2006.01)
  *A61B 3/15* (2006.01)
(52) U.S. Cl.
  CPC .............. *A61B 3/12* (2013.01); *A61B 3/0083* (2013.01); *A61B 3/0091* (2013.01); *A61B 3/152* (2013.01); *A61B 3/156* (2013.01)

(58) Field of Classification Search
  CPC ......... A61B 3/12; A61B 3/152; A61B 3/0083; A61B 3/0091; A61B 3/156; A61B 3/14; A61B 3/13; A61B 3/145
  (Continued)

(56) References Cited

U.S. PATENT DOCUMENTS 5,371,558 A * 12/1994 Kohayakawa ......... A61B 3/152
                                                    351/206
5,568,208 A * 10/1996 Van de Velde ...... A61B 3/1025
                                                    351/205
(Continued)

FOREIGN PATENT DOCUMENTS

WO      2010113193 A1    10/2010
WO      2012041723 A1    4/2012
WO    WO 2012041723 A1 * 4/2012 ............. A61B 3/152

OTHER PUBLICATIONS

Intrnational Search Report dated Aug. 26, 2014.

*Primary Examiner* — Stephone B Allen
*Assistant Examiner* — Rahman Abdur
(74) *Attorney, Agent, or Firm* — Hedman & Costigan, P.C.; James V. Costigan; Kathleen A. Costigan

(57) ABSTRACT

Ocular fundus inspection apparatus (10) having a frame (11) provided with references for the positioning of at least one of the patient's eyes in an inspection position, and an inspection unit (100) fixed to the frame (11) and comprising:
  a first optical unit (12) having an optical axis incident in correspondence of the inspection position references;
  an image detecting device (13);
  a second optical unit (14), for the focusing, having an optical axis incident on the detecting device (13), in said inspection unit (100) being defined an optical path between the first optical unit (12) and the detecting device (13);

(Continued)

a first lighting unit (15) for projecting a focusing pattern, for focusing the ocular fundus on said detecting device (13), the focusing pattern being formed by an infrared radiation.

The first lighting unit (15) emits the focusing pattern from a first emission position.

11 Claims, 4 Drawing Sheets

(58) Field of Classification Search
USPC .................. 351/207, 209, 210, 212, 213
See application file for complete search history.

(56) References Cited

U.S. PATENT DOCUMENTS

| | | | |
|---|---|---|---|
| 2011/0299034 A1* | 12/2011 | Walsh ................ | A61B 3/102 351/206 |
| 2012/0062842 A1* | 3/2012 | Griggio .............. | A61B 3/0091 351/209 |
| 2012/0224141 A1* | 9/2012 | Ichikawa ............ | A61B 3/12 351/206 |
| 2012/0229765 A1* | 9/2012 | Makihira ............ | A61B 3/102 351/206 |

\* cited by examiner

APPARATUS FOR OCULAR FUNDUS INSPECTION

The present finding relates to an ocular fundus inspection apparatus.

In particular, the present ocular fundus inspection apparatus falls within the category of apparatuses suitable for vision and for photographic reproduction of the ocular fundus.

The present ocular fundus inspection apparatus is especially suitable for vision and/or photographic reproduction of the retina.

Therefore the present invention takes its place in the field of the eye inspection optical devices.

Nowadays, in the field of ocular fundus inspection apparatuses a traditional apparatus is known, in particular, which allows focusing the ocular fundus using a near-infrared radiation.

This radiation for focusing is not visible to the patient so that the pupil constriction, which otherwise would be induced by a visible intense light, is prevented.

In detail, this traditional ocular fundus inspection apparatus comprises an optical head faced to a face support on which resting the face.

When the face is rested on the face support, one eye is in a predefined position of inspection which is faced to the optical head.

Inside the optical head, it is provided an image detecting device before which there are placed two optical units which are coaxial and define a main optical axis incident in correspondence to the inspection position references.

A first of these optical units, which is placed between the detecting device and the second optical unit is suitable for focusing the ocular fundus on the detecting device and, to this aim, is equipped with a lens movable along the main optical axis.

For lighting the ocular fundus a lighting device is provided which has a secondary optical axis transverse and intersecting the main optical axis.

This lighting device comprises, aligned along the secondary optical axis, a lamp suitable for producing a visible light and an IR emitter suitable for irradiating the ocular fundus for the focusing.

At the intersection of the main optical axis with the secondary optical axis a reflection device is arranged suitable for reflecting the radiation produced by the lamp and/or the IR emitter towards the inspection position references.

Between the IR emitter and the reflection device a transparent small plate is placed provided with a reference mark obtained by a visible radiation permeable and IR radiation opaque covering.

The image quality of the reference mark, reflected by the ocular fundus and which is formed on the detecting device, indicates whether or not the ocular fundus is conjugated with the detecting device, i.e. whether or not it is focused.

This reference mark image is not clear when the ocular fundus is not focused.

For the focusing, the movable lens of the first optical unit is moved along the main optical axis until obtaining a clear image of the reference mark.

The transparent small plate is synchronously moved with the movable lens for keeping the detecting device conjugated with the small plate.

A drawback of this traditional ocular fundus inspection apparatus is that it is structurally complex to guarantee the synchronous movement of the small plate and of the movable lens.

Furthermore, a problem which we are particularly aware of in the field of the traditional ocular fundus inspection apparatuses is related to the fact that the eye to be inspected can change its optical alignment during inspection or during focusing, for instance following to the patient's conscious or unconscious movements.

In fact, if the patient moves his/her eyes focusing points at a different distance from his/her eye, the crystalline lens changes its alignment and determines a focusing loss of the ocular fundus relative to the detecting device.

The underlying problem of the present invention is to simplify the structure of the traditional ocular fundus inspection apparatus.

The main task of the present finding consists in realizing an ocular fundus inspection apparatus which finds a solution to such problem solving the complained drawbacks of the above described ocular fundus inspection apparatus.

Within the scope of such task it is the aim of the present finding to propose an ocular fundus inspection apparatus which, relative to the traditional one, has a smaller size in transverse direction relative to the main optical axis.

Another aim of the present finding consists in realizing an ocular fundus inspection apparatus employing fewer optical components, i.e. lenses or optical units, relative to the described traditional ocular fundus inspection apparatus.

Further an aim of the finding consists in proposing an ocular fundus inspection apparatus which is of easier maintenance relative to the above described traditional ocular fundus inspection apparatus.

A further aim of the finding consists in proposing an ocular fundus inspection apparatus which allows obtaining retinal fundus photographic images more quickly than the traditional ocular fundus inspection apparatuses.

Another further aim of the finding consists in proposing an ocular fundus inspection apparatus which allows obtaining retinal fundus photographic images more efficiently than the traditional ocular fundus inspection apparatuses.

This task, as well as these and other aims which will better appear afterwards are reached by an ocular fundus inspection apparatus according to the herein enclosed claim 1.

Detailed characteristics of the ocular fundus inspection apparatus according to the finding are reported in the dependent claims.

Further characteristics and advantages of the finding will come out much more from the description of one preferred, but not exclusive, embodiment of the ocular fundus inspection apparatus according to the finding, illustrated for indicative and not limitative purpose in the attached sheets of drawings, wherein.

Figure 1:
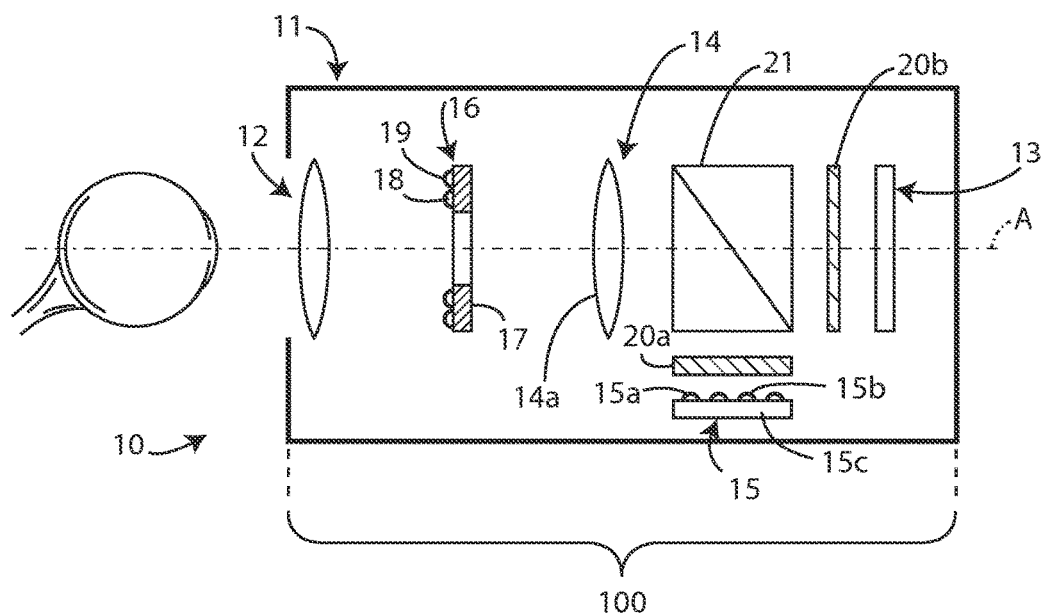
FIG. 1 illustrates a simplified scheme of a detail of an ocular fundus inspection apparatus according to the finding concerning an inspection unit faced to a stylized eye to be inspected.

With particular reference to the cited Figures, an ocular fundus inspection apparatus suitable for vision and for photographic reproduction of the ocular fundus is overall designated by 10.

The present ocular fundus inspection apparatus 10 is especially suitable for vision and/or photographic reproduction of the retina.

Structurally, the ocular fundus inspection apparatus 10 comprises a frame 11 provided with references for the positioning of at least one of the user's eyes in an inspection position, and an inspection unit 100 fixed to the frame 11.

Such references can be constituted by a traditional face support, in case adjustable relative to the frame 11 and shaped so that the user, once has rested his/her face on the face support, presents his/her eye, or his/her eyes, in said inspection position.

The inspection unit 100 comprises:
a first optical unit 12 having an optical axis incident on the inspection position references;
an image detecting device 13;
a second optical unit 14, for the focusing, having an optical axis incident on the detecting device 13.

Preferably the second optical unit 14 comprises at least one lens 14a movable along the optical axis of the second optical unit 14 for focusing the ocular fundus on the detecting device 13.

In the inspection unit 100 an optical path is arranged between the first optical unit 12 and the detecting device 13, which passes through the second optical unit 14.

The optical axis of the second optical unit 14 is preferably coincident with the optical axis of the first optical unit 12, and defines a main optical axis A of the inspection unit 100.

The inspection unit 100 also comprises a first lighting unit 15 suitable for projecting, towards the inspection position references, a focusing or focalization pattern, susceptible of serving as a reference for focusing the ocular fundus on the detecting device 13, in a per se traditional way.

Said focusing pattern is formed by an infrared radiation and in particular by a near-infrared radiation, i.e. having a wavelength substantially comprised between 700 nm and 980 nm.

According to the finding, the ocular fundus inspection apparatus 10 presents a particular characteristic in that the first lighting unit 15 emits said focusing pattern from a first emitting position which is placed between the second optical unit 14 and said detecting device 13.

Thus, in the ocular inspection apparatus 10 it is avoided to have to move the source of the focusing pattern synchronously with the focusing lens as it happens in traditional apparatuses, since, according to the finding, the projecting optical path of the focusing pattern, jargon denominated as projection path, and the path of the image to be obtained, jargon denominated as imaging path, are in common for the distance extending between the ocular fundus and the above mentioned first position.

The first lighting unit 15 advantageously comprises:
first lighting means 15a suitable for projecting said focusing pattern;
second lighting means 15b suitable for projecting a luminous signal towards said inspection position, said luminous signal being formed by visible light and suitable for being fixed by the eye to be inspected for maintaining stable the optical alignment of the latter. Preferably the first and second lighting means 15a and 15b are fixed to a support 15c and they have a direction of luminous emission transverse to the optical axis of the second optical unit 14.

At the intersection between said emission direction and the optical axis of the second optical unit 14, it is advantageously provided a splitter of luminous beams, jargon denominated as beam splitter, which is designated in the Figures by reference 21.

This beam splitter 21 is placed in said first emission position and is suitable for addressing to the second optical unit 14 the luminous radiation coming from the first and second lighting means 15a and 15b, and for addressing to the detecting device 13 the luminous radiation coming from the second optical unit 14.

Figures 2A, 2B:
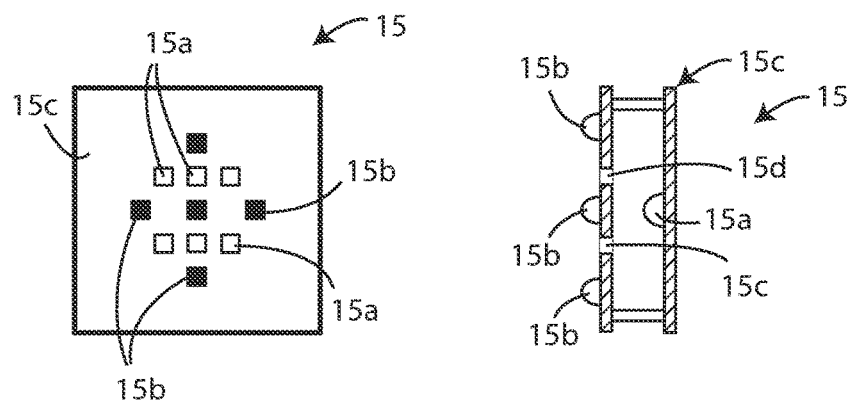
FIGS. 2a and 2b illustrate two alternative variants of a detail of the ocular fundus inspection apparatus of FIG. 1, concerning the first lighting unit.

With particular reference to FIG. 2a, the first and second lighting means 15a and 15b are advantageously realized by led chips on board assembled directly on support 15c.

In such case a plurality of alternative focusing patterns can be realized, operating selectively some of the led chips on board forming the first lighting means 15a.

Alternatively, according to FIG. 2b, the support can consist of two supporting plates, a front one supporting the second lighting means 15b, and a rear one supporting the first lighting means 15a.

On the above mentioned front plate some slits 15c are realized suitable for conveying, in luminous beams, the light produced by the first lighting means 15a.

In practice, when the patient stares at the luminous signal generated by the second lighting means 15b, he/she keeps his/her eye steady both in orientation and focalization, and thus the possibility of inspecting the ocular fundus more quickly and efficiently is obtained.

Preferably, the second lighting means 15b allow emitting the luminous signal from a plurality of different predefined positions—exemplified in FIG. 2a by full black squares—so as to be able to induce the same number of different orientations of the eye that is staring at the luminous signal switched on.

The inspection unit 100 advantageously comprises also a second lighting unit 16 suitable for projecting a luminous beam from a second emission position, said luminous beam being directed towards said inspection position and being selectively formed of:
a visible or infrared light suitable for lighting the ocular fundus for obtaining an image of the latter reflected on the detecting device 13;
an alignment pattern, consisted of an infrared radiation functional to the alignment of the inspection apparatus 10 to the eye to be inspected.

Said second emission position is advantageously placed between the first optical unit and the second optical unit.

Preferably, the second lighting unit 16 is faced to the first optical unit 12 for projecting, through the latter, said alignment pattern.

Effectively the image of the alignment pattern, seen on the ocular fundus by the detecting device 13, provides information on the correct distance of the inspection unit 100 relative to the eye to be inspected and on the position of the optical axis of the latter relative to the optical axis of the first optical unit 12.

In particular, if the pupil and the second lighting unit 16 are not conjugated relative to the first optical unit 12, the image of the alignment pattern, seen by the detecting device 13 on the ocular fundus, is blurred.

The inspection apparatus 10 advantageously comprises an electronic device suitable for processing an image of the alignment pattern detected by the detecting device 13 and consequently for adjusting, in a per se traditional way, the reciprocal position of the inspection unit 100 and of the eye to be inspected.

Preferably, the frame 11 comprises:

a base 11a provided with said references;

an optical head 11b, to which is fixed the inspection unit 100;

driving means for moving, preferably according to 3 axes, the optical head 11b relative to the base 11a for aligning the latter to the eyes to be inspected.

Advantageously, the above mentioned electronic device is connected to the above mentioned driving means for driving the positioning of the optical head 11b relative to the base 11a.

The lighting unit 16 preferably comprises:

a support 17 fixed to the frame 11 between the first optical unit 12 and the second optical unit 14, and having an operating part B, permeable to the luminous radiation or perforated, intersected by the main optical axis A;

third lighting means 18 fixed to the support 17, suitable for emitting visible or infrared light, for obtaining an ocular fundus image reflected on said detecting device 13;

fourth lighting means 19 fixed to the support 17, suitable for projecting said alignment pattern.

Advantageously, also the third and fourth lighting means 18 and 19 comprise led chips on board.

The ocular fundus inspection apparatus 10 advantageously comprises means of optical filtering suitable for shielding the detecting device 13 from light not coming from the ocular fundus to be inspected.

In a first embodiment, said filtering means are part of the inspection unit 100 and preferably are selected between:

polarized optical filters 20a, 20b, and a polarized beam splitter 21, suitable for eliminating or at least attenuating possible reflexes which can be due to the fact that the imaging path and the projecting path are in a large part coincident.

Polarized filters 20a and 20b advantageously comprise:

a first optical filter 20a, permeable to a light having a first polarization and impermeable to a light having a second polarization, placed in front of the first lighting unit 15;

a second optical filter 20b, permeable to a light having said second polarization and impermeable to a light having said first polarization, placed in front of the detecting device 13.

The beam splitter 21 is advantageously polarized to allow the passage of a light beam, having a given polarization, from the first lighting unit 15 to said inspection position, and contextually prevent the passage of a light having said given polarization towards the detecting device 13.

Effectively, the above mentioned filtering means eliminate the polarized light which is reflected towards the detecting device 13 from the optical components and from the cornea, allowing instead the passage, towards the detecting device 13, of the light which is reflected from the ocular fundus, since such light is depolarized.

With particular reference to Figures from 5a to 5d, in these Figures there are schematised alternative embodiments of the finding which differ because of alternative embodiments of said filtering means.

Figure 5A:
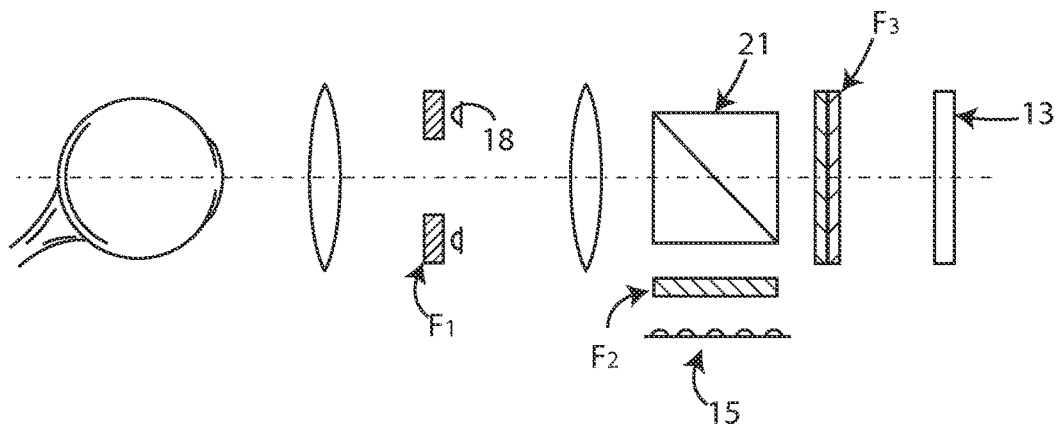
FIGS. 5a, 5b, 5c and 5d illustrate alternative simplified schemes of an ocular fundus inspection apparatus according to the finding.

In particular, according to FIG. 5a said filtering means advantageously comprise:

a first filter F1 permeable to a visible light having a first polarization and impermeable to a visible light having a second polarization, placed in front of said third lighting means 18;

a second filter F2 permeable to an infrared light having a third polarization and impermeable to an infrared light having a fourth polarization, placed in front of said first lighting unit;

a third optical filter F3, permeable to a visible light having said second polarization and to an infrared light having said fourth polarization and impermeable to a visible light having said first polarization and to an infrared light having said third polarization, placed in front of the detecting device 13.

Figure 5B:
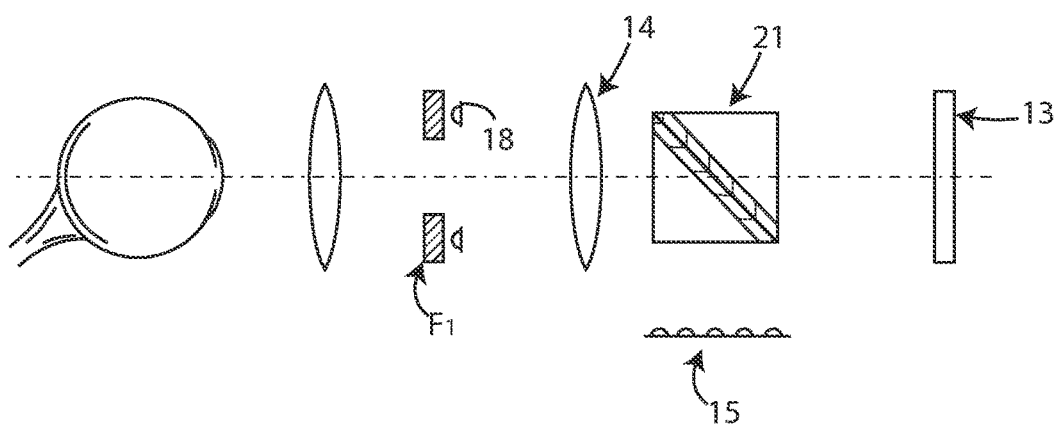

As an alternative, according to FIG. 5b, said filtering means advantageously comprise:

a first filter F1 permeable to a visible light having a first polarization and impermeable to a visible light having a second polarization, placed in front of said third lighting means 18;

the beam splitter 21 which is polarized in order to be permeable to a visible light having said second polarization and to an infrared light having a third polarization and impermeable to a visible light having said first polarization and to an infrared light having said fourth polarization different from said third polarization.

Figure 5C:
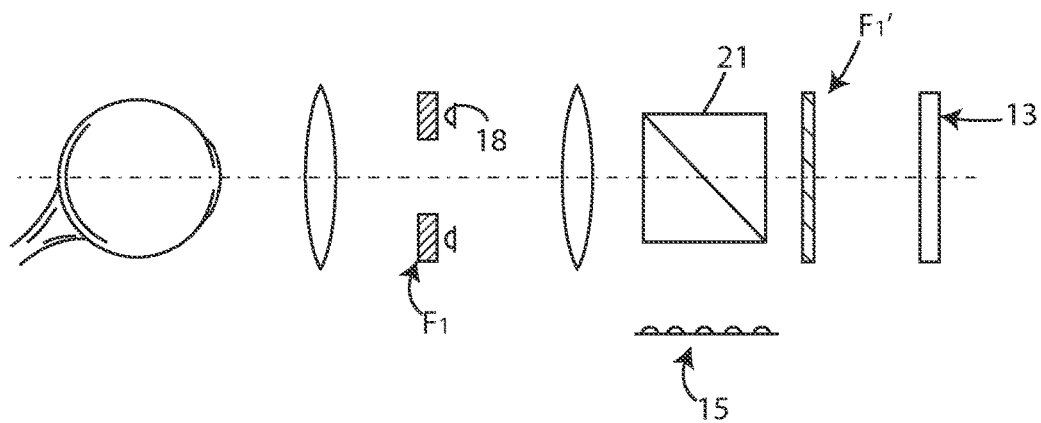

Again, in another alternative, illustrated in FIG. 5c, said filtering means advantageously comprise:

a first filter F1 permeable to a visible light having a first polarization and impermeable to a visible light having a second polarization, placed in front of said third lighting means 18;

a second filter F1' also permeable to a visible light having said second polarization and impermeable to a visible light having said first polarization, placed in front of the detecting device 13.

In a variant of this last solution it is possible to provide a further optical unit interposed between the second filter F1' and the detecting device 13.

Figure 5D:
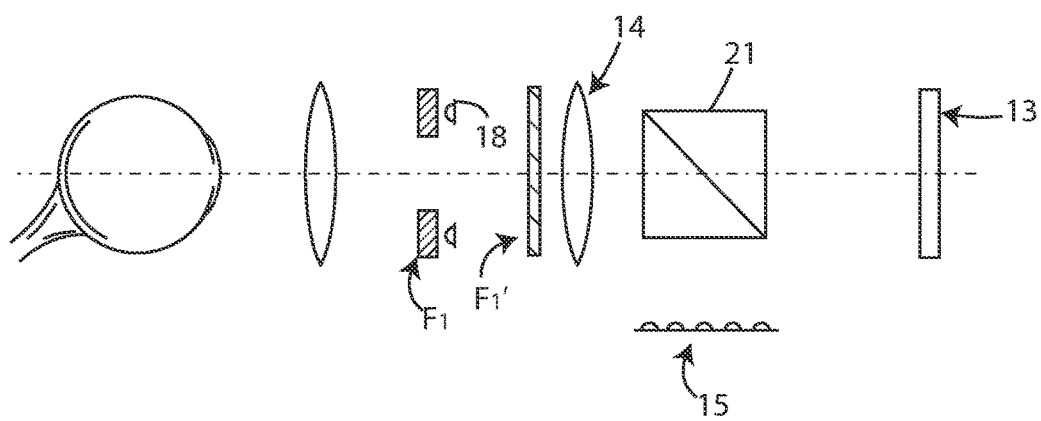

In another further alternative, illustrated in FIG. 5d said filtering means advantageously comprise:

a first filter F1 permeable to a visible light having a first polarization and impermeable to a visible light having a second polarization different from said first polarization, placed in front of said third lighting means 18;

a second filter F1' also permeable to a visible light having said second polarization and impermeable to a visible light having said first polarization, placed in front of the second optical unit 14.

Figure 3:
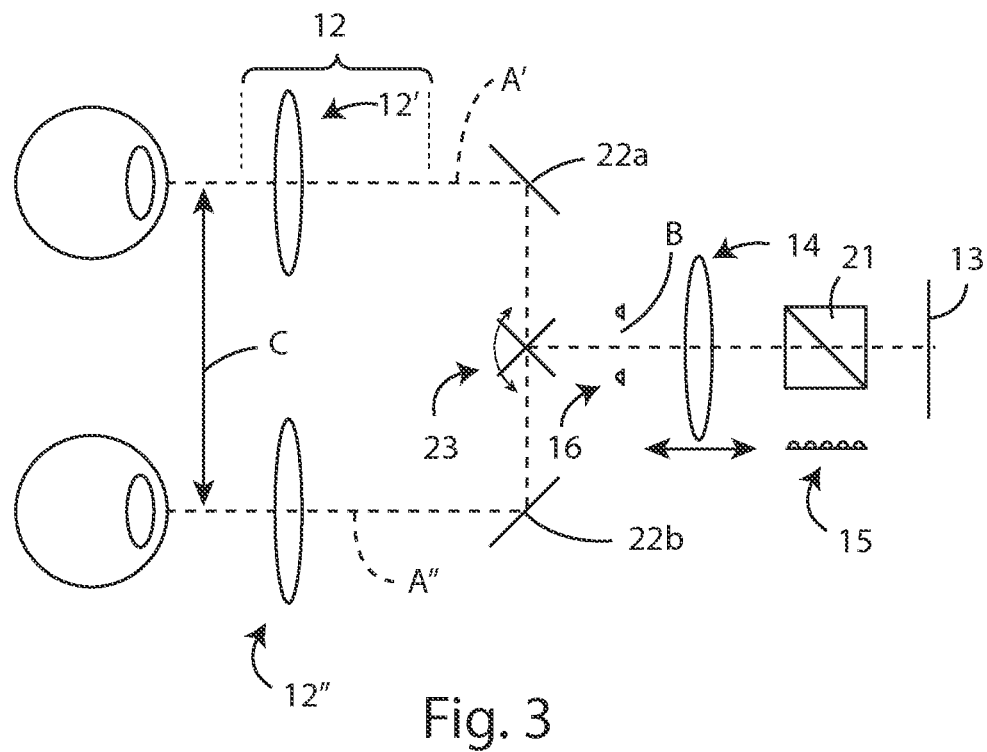
FIG. 3 illustrates a simplified scheme of a first variant of the ocular fundus inspection apparatus according to the finding.
Figure 4:
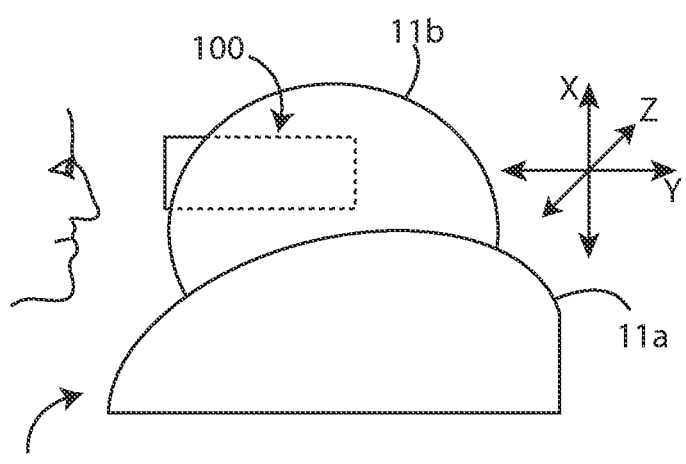
FIG. 4 illustrates a simplified scheme of an ocular fundus inspection apparatus.

In a first embodiment variant of the finding, illustrated by way of example and not as a limitation in FIG. 3, the inspection apparatus 10 advantageously comprises two first optical units 12' and 12" placed side by side, spaced one from each other and faced to two inspection positions for inspecting two different eyes.

There are, furthermore, advantageously provided reflection means placed between the first optical units 12' and 12" and the second optical unit 14 for realizing two alternative optical path branches A' and A" extending between the second optical unit 14 and the first optical units 12' and 12".

Preferably, driving means are provided for adjusting the reciprocal distance C between the two first optical units 12' and 12", so as to adapt such distance C to the distance which separates the eyes to be inspected.

Preferably, said reflection means comprise two fixed mirrors 22a and 22b placed each one to intercept a corresponding one of the optical axes of the first optical units 12' and 12";

a movable mirror 23 placed to intercept the optical axis of the second optical unit 14 and selectively orientable towards one of the fixed mirrors 22*a* and 22*b* for addressing light to, or for receiving light from, said fixed mirrors 22*a* and 22*b*.

Effectively, the two first optical units 12' and 12" are aligned each one to a corresponding eye preferably in succession, as described hereinafter.

For aligning the first one 12' of the first optical units 12' and 12" to the corresponding eye, preliminarily the movable mirror 23 is placed in a first configuration, in which it reflects towards the first fixed mirror 22*a* and towards the detecting device 13, then the first one 12' of the first optical units 12' and 12" is aligned to the corresponding eye, in a per se traditional way.

Subsequently, for aligning the second one 12" of the first optical units 12' and 12" to the corresponding eye, the movable mirror 23 is preliminarily oriented in a second configuration in which it reflects towards the second fixed mirror 22*b* and towards the detecting device 13, then, the alignment of the second one 12" of the first optical units 12' and 12" to the corresponding eye is carried out, in a per se traditional way, having care of not modifying the alignment of the first one 12' of the first optical units 12' and 12" to its corresponding eye.

Afterwards, the image detection of the ocular fundus of both eyes is carried out, in rapid succession, by means of a rapid transition of the movable mirror from the first one to the second one of said configurations, or vice versa.

An inspection apparatus 10, according to the finding allows acquiring, as aforementioned, the ocular fundus image of both eyes of a patient in a negligible range of time, i.e. in a time less than that of reaction of the patient's eye.

In other words, the elapsing time between the two successive acquisitions of the ocular fundus images preferably is less than 100 ms, i.e. less than that which would be necessary to the patient for perceiving two successive flashes produced by the third lighting means 18 for lighting the ocular fundus to be photographed.

In an alternative embodiment of the finding, the optical units 12' and 12" are at a fixed distance.

According to such embodiment, first the alignment of the first ocular unit 12' to a first eye is realized, and then the photograph of the first eye is taken.

Subsequently the alignment of the second ocular unit 12" to the second eye is realized and a photograph of the second eye is taken.

Such embodiment has the advantage of allowing a simplified structure which does not provide adjusting means of the reciprocal distance between the two optical units 12' and 12" even at the same time reducing the alignment run of the optical head 11*b* to the eyes to be photographed, thanks to the fact of providing two optical units instead of a single optical unit to be employed for reproducing the fundus of both eyes.

In this way the acquisition of ocular fundus images becomes greatly faster and less annoying for the patient.

Advantageously in a second embodiment variant of the finding, preferred but not exclusive, the inspection apparatus 10 comprises two inspection units 100 side by side, and faced to two inspection positions for contemporaneously, or in rapid succession, inspecting two different eyes.

Preferably driving means for adjusting the relative distance among the inspection units 100 and for adapting such distance to the distance between the eyes to be inspected are provided.

By means of said second embodiment variant of the finding, it is possible to simultaneously and independently acquire, by the respective inspection units 100, the ocular fundus images of both eyes of the patient.

An ocular fundus inspection apparatus according to the present finding achieves therefore the aforesaid task and aims, in particular it is structurally easier than the traditional ocular fundus inspection apparatuses.

Furthermore, an ocular fundus inspection apparatus according to the finding has a smaller size in transverse direction relative to the main optical axis, relative to the traditional ocular fundus inspection apparatuses, and allows employing fewer optical components, i.e. lenses or optical units all to the advantage of the simplicity of assembly, of maintenance and so of the overall production and management costs. An ocular fundus inspection apparatus according to the finding presents also the advantage of having fewer movable components relative to the traditional ones, thus reducing the risk of malfunctions or breakdowns.

A further advantage of the ocular inspection apparatus according to the finding, relative to the traditional ones is that it allows obtaining photographic images of the retinal fundus in a faster, more efficient and less annoying way for the patient.

An ocular fundus inspection apparatus according to the finding is also easily assemblable and allows avoiding complex calibrations thanks to the fact of providing third lighting means and fourth lighting means coaxial to the main optical axis.

The finding so conceived is susceptible of numerous modifications and variants, all falling within the scope of protection of the enclosed claims.

Furthermore, all details may be replaced by other technically equivalent elements.

In practice, the employed materials, as well as the contingent shapes and sizes, may be changed according to the contingent requirements and the state of the art.

Where the structural characteristics and the techniques mentioned in the following claims are followed by marks or numbers of reference, such marks or numbers of reference have been affixed with the only aim of increasing the intelligibility of the claims themselves and, accordingly, they do not represent in any way a limitation to the interpretation of each element identified, merely by way of example, by such marks or numbers of reference.

The invention claimed is:

1. An ocular fundus inspection apparatus (10) comprising a frame (11) provided with references of the positioning of at least one of a patient's eyes in an inspection position, and an inspection unit (100) fixed to said frame, the apparatus (10) comprising:
   a first optical unit (12) having an optical axis incident in correspondence of said inspection position;
   an image detecting device (13);
   a second optical unit (14), configured for focusing, having an optical axis incident on said detecting device (13), in said inspection unit (100) where said optical axis incident on said detecting device (13) defines an optical path between said first optical unit (12) and said detecting device (13), through said second optical unit (14);
   a first lighting unit (15) configured to project, towards said inspection position, a focusing pattern to serve as a reference for focusing the ocular fundus on said detecting device (13), said focusing pattern being formed by an infrared radiation; wherein the first lighting unit (15) emits said focusing pattern from a first emission position which is placed between said second optical unit (14) and said detecting device;

where said first lighting unit (15) comprises:
first lighting means (15a) configured to project said focusing pattern formed by infrared radiation;
second lighting means (15b) configured to project a luminous signal towards said inspection position, said luminous signal being formed by visible light and configured to be fixed by the eye to be inspected for stably maintaining an optical alignment of said second lighting means (15b) said first lighting means (15a) and said second lighting means (15b) being fixed to a common support (15c), said first lighting means (15a) and said second lighting means (15b) being positioned so that they both focus on a same beam splitter (21), said first lighting means (15a) and said second lighting means (15b) have a direction of luminous emission transverse to an optical axis of a second optical unit.

2. The ocular fundus inspection apparatus (10) according to claim 1 wherein said inspection unit (100) comprises a second lighting unit (16) configured to project a luminous beam from a second emission position, said luminous beam being addressed towards said inspection position and being selectively formed by:
a visible or infrared light suitable for lighting the ocular fundus for obtaining an image of the latter reflected on said detecting device (13);
an alignment pattern, comprised of an infrared radiation for the alignment of said inspection apparatus (10) to the eye to be inspected;
said second emission position being placed between said first optical unit (12) and said second optical unit (14).

3. The ocular fundus inspection apparatus (10) according to claim 2 wherein said second lighting unit (16) comprises:
a support (17) fixed to said frame (11) between said first optical unit (12) and said second optical unit (14), and having an operating part (B), permeable to the luminous radiation or perforated, intersected by said main optical axis (A);
third lighting means (18) fixed to said support (17), configured to emit visible or infrared light, for obtaining an image of the ocular fundus reflected on said detecting device (13);
fourth lighting means (19) fixed to said support (17), configured to project said alignment pattern.

4. The ocular fundus inspection apparatus (10) according to claim 1 wherein said first lighting means and said second lighting means comprise LED chips on a board.

5. The ocular fundus inspection apparatus (10) according to claim 1 further comprising means of optical filtering suitable for shielding said detecting device (13) from light not coming from the ocular fundus to be inspected.

6. The ocular fundus inspection apparatus (10) according to claim 1 wherein said first optical unit (12) comprises two first optical units (12, 12") placed side by side, spaced and faced to two inspection positions for inspecting two different eyes, reflecting means being provided placed between said first optical units (12', 12") and said second optical unit (14) for realizing two optical path alternative branches extending between said second optical unit (14) and said first optical units (12, 12").

7. Inspection apparatus according to claim 6 wherein said reflecting means comprise:
two fixed mirrors (22a and 22b) each one positioned to intercept a corresponding one of the optical axes of said first optical units (12' and 12");
a movable mirror (23) to intercept the optical axis of said second optical unit (14) and selectively orientable towards one of said fixed mirrors (22a and 22b) for addressing light to, or for receiving light from, said fixed mirrors (22a, 22b).

8. The inspection apparatus according to claim 6 wherein said reflecting means comprise:
two fixed mirrors (22a and 22b) each one placed to intercept a corresponding one of the optical axes of said first optical units (12 and 12");
a movable mirror (23) to intercept the optical axis of said second optical unit (14) and selectively orientable towards one of said fixed mirrors (22a and 22b) for addressing light to, or for receiving light from, said fixed mirrors (22a, 22b).

9. The ocular fundus inspection apparatus (10) according to claim 1 further comprising two inspection units side by side and faced to two inspection positions, for contemporaneously, or in rapid succession, inspecting two different eyes.

10. An ocular fundus inspection apparatus (10) comprising a frame (11) provided with references of the positioning of at least one of a patient's eyes in an inspection position, and an inspection unit (100) fixed to said frame and comprising:
a first optical unit (12) having an optical axis incident in correspondence of said inspection position;
an image detecting device (13);
a second optical unit (14), for the focusing, having an optical axis incident on said detecting device (13), in said inspection unit (100) being defined an optical path between said first optical unit (12) and said detecting device (13), through said second optical unit (14);
a first lighting unit (15) suitable for projecting, towards said inspection position, a focusing pattern, susceptible of serving as a reference for focusing the ocular fundus on said detecting device (13), said focusing pattern being formed by an infrared radiation; characterized in that the first lighting unit (15) emits said focusing pattern from a first emission position which is placed between said second optical unit (14) and said detecting device on a beam splitter (21), said first lighting unit (15) has a direction of luminous emission transverse to an optical axis of said second optical unit (14);
wherein said first optical unit (12) comprises two first optical units (12', 12") placed side by side, spaced apart and faced to two inspection positions for inspecting two different eyes, wherein said ocular fundus inspection device also comprises reflecting means being provided between said first optical units (12', 12") and said second optical unit (14) for realizing two optical path alternative branches extending between said second optical unit (14) and said first optical units (12', 12");
wherein the reciprocal distance (C) between the two optical units (12', 12") is adaptable to the distance which separates the eyes to be inspected which separates the eyes to be inspected;
wherein said reflecting means comprise:
two fixed mirrors (22a and 22b) placed each one to intercept a corresponding one of the optical axes of said first optical units (12' and 12");
a movable mirror (23) placed to intercept the optical axis of said second optical unit (14) and selectively orientable towards one of said fixed mirrors (22a and 22b) for addressing light to, or for receiving light from, said fixed mirrors (22a, 22b).

11. An ocular fundus inspection apparatus (10) comprising a frame (11) provided with references of the positioning of at least one of a patient's eyes in an inspection position, and an inspection unit (100) fixed to said frame, the apparatus (10) comprising:

a first optical unit (12) having an optical axis incident in correspondence of said inspection position;

an image detecting device (13);

a second optical unit (14), configured for focusing, having an optical axis incident on said detecting device (13), in said inspection unit (100) where said optical axis incident on said detecting device (13) defines an optical path between said first optical unit (12) and said detecting device (13), through said second optical unit (14);

a first lighting unit (15) configured to project, towards said inspection position, a focusing pattern to serve as a reference for focusing the ocular fundus on said detecting device (13), said focusing pattern being formed by an infrared radiation; wherein the first lighting unit (15) emits said focusing pattern from a first emission position which is placed between said second optical unit (14) and said detecting device;

where said first lighting unit (15) comprises:

first lighting means (15a) configured to project said focusing pattern formed by infrared radiation;

second lighting means (15b) configured to project a luminous signal towards said inspection position, said luminous signal being formed by visible light and configured to be fixed by the eye to be inspected for stably maintaining an optical alignment of said second lighting means (15b) said first lighting means (15a) and said second lighting means (15b) being fixed to a common support (15c), said first lighting means (15a) and said second lighting means (15b) being positioned so that they both focus on a same beam splitter (21), said first lighting means (15a) and said second lighting means (15b) have a direction of luminous emission transverse to an optical axis of a second optical unit; said inspection unit (100) comprises a second lighting unit (16) configured to project a luminous beam from a second emission position, said luminous beam being addressed towards said inspection position and being selectively formed by:

a visible or infrared light suitable for lighting the ocular fundus for obtaining an image of the latter reflected on said detecting device (13);

an alignment pattern, comprised of an infrared radiation for the alignment of said inspection apparatus (10) to the eye to be inspected;

said second emission position being placed between said first optical unit (12) and said second optical unit (14); said second lighting unit (16) comprises:

a support (17) fixed to said frame (11) between said first optical unit (12) and said second optical unit (14), and having an operating part (B), permeable to the luminous radiation or perforated, intersected by said main optical axis (A);

third lighting means (18) fixed to said support (17), configured to emit visible or infrared light, for obtaining an image of the ocular fundus reflected on said detecting device (13); and fourth lighting means (19) fixed to said support (17), configured to project said alignment pattern.

* * * * *